Figure 1:
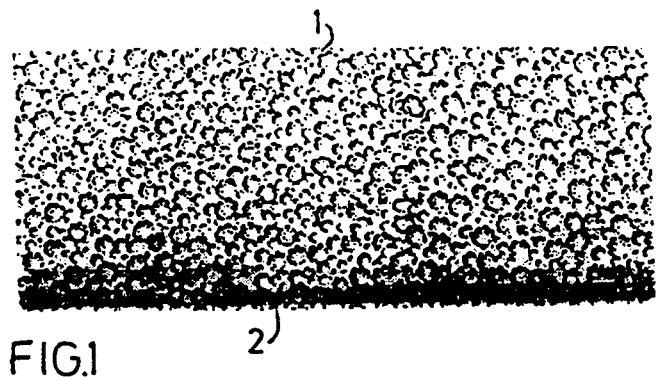

United States Patent [19]

Hellgren et al.

[11] Patent Number: 5,391,161
[45] Date of Patent: Feb. 21, 1995

[54] ABSORPTION MATERIAL, PREFERABLY FOR USE IN DISPOSABLE ARTICLES SUCH AS DIAPERS, SANITARY NAPKINS OR WOUND DRESSINGS

[75] Inventors: Maud Hellgren, Mölnlycke; Henry Zöller, Frölunda, both of Sweden

[73] Assignee: Molnlycke AB, Goteborg, Sweden

[21] Appl. No.: 970,959

[22] Filed: Nov. 3, 1992

Related U.S. Application Data

[63] Continuation of Ser. No. 866,096, Apr. 6, 1992, abandoned, which is a continuation of Ser. No. 201,275, May 23, 1988, abandoned, which is a continuation of Ser. No. 866,100, Jul. 16, 1986, abandoned.

[30] Foreign Application Priority Data

Jul. 31, 1985 [JP] Japan ................. 60-169625

[51] Int. Cl.$^6$ ............................. A61F 13/15
[52] U.S. Cl. .................. 604/366; 604/368; 604/374; 428/212; 428/213; 428/218; 428/280; 428/281; 428/282; 428/284; 428/296; 428/913
[58] Field of Search .......... 604/366, 368, 374; 428/212, 213, 218, 280-282, 284, 288, 296, 913

[56] References Cited

U.S. PATENT DOCUMENTS

| 3,903,889 | 9/1975 | Torr, deceased . | |
|---|---|---|---|
| 4,103,062 | 7/1978 | Aberson et al. | 604/368 |
| 4,160,059 | 7/1979 | Samejima . | |
| 4,381,783 | 5/1983 | Elias . | |
| 4,544,596 | 10/1985 | Holtman . | |
| 4,595,567 | 6/1986 | Hedrick . | |
| 4,610,678 | 9/1986 | Weisman et al. | 604/368 |
| 4,699,823 | 10/1987 | Kellenberger et al. | 604/378 |
| 4,818,315 | 4/1989 | Hellgren et al. | 428/218 |
| 4,980,226 | 12/1990 | Hellgren et al. | 428/218 |

FOREIGN PATENT DOCUMENTS

| 0108637 | 5/1984 | European Pat. Off. . |
| 0122042 | 10/1984 | European Pat. Off. . |
| 0169184 | 1/1986 | European Pat. Off. . |
| 2525210 | 12/1976 | Germany . |
| 55-16611 | 2/1980 | Japan . |
| 60-198152 | 10/1985 | Japan . |
| 1399153 | 6/1975 | United Kingdom . |
| 2015604 | 9/1979 | United Kingdom . |
| 2061339 | 5/1981 | United Kingdom . |
| 2131699 | 6/1984 | United Kingdom . |
| 2165757 | 4/1986 | United Kingdom . |
| WO80/01455 | 7/1980 | WIPO . |
| WO83/01965 | 6/1983 | WIPO . |
| WO86/01400 | 3/1986 | WIPO . |

Primary Examiner—Randall L. Green
Assistant Examiner—Mary Beth Jones
Attorney, Agent, or Firm—Young & Thompson

[57] ABSTRACT

An absorption material, preferably for use in disposable articles such as diapers, sanitary napkins or wound dressings, comprises 70-95% of at least one type of absorbing fibers, 2-20% of bonding fibers activated by heat, and 2-25% of a highly absorbent material, the absorption fibers and the highly absorbent material having been bonded into a coherent body by means of the binding fibers.

2 Claims, 1 Drawing Sheet

ABSORPTION MATERIAL, PREFERABLY FOR USE IN DISPOSABLE ARTICLES SUCH AS DIAPERS, SANITARY NAPKINS OR WOUND DRESSINGS

This application is a continuation, of application Ser. No. 07/866,096, filed Apr. 6 1992, now abandoned, which is a continuation of Ser. No. 07/201,275, filed May 23 1988, now abandoned, which is a continuation of Ser. No. 06/886,100, of Jul. 16, 1986, now abandoned.

The present invention relates to an absorption material, preferably for use in disposable articles such as diapers, sanitary napkins or wound dressings.

The determining factor with regard to function and economy of absorbent articles such as sanitary napkins, diapers, incontinence articles, tampons, etc. is the amount of absorption material required to absorb a certain quantity of fluid in relation to the intended use of the specific absorbent article. In most cases it is further of vital importance to bind the fluid, thereby preventing it from being pressed out under the influence of the stresses placed on the article during its use.

In order to overcome the problem of liquid-containing capacity in absorbent articles, efforts have been made to utilize so-called super absorbents. Because of their poor liquid-transmitting properties, however, it has proved difficult to take advantage of the otherwise high liquid-retaining potential of these super absorbents.

Furthermore, the costs involved in producing absorption materials with the aid of super absorbents are considerably higher than those connected to the use of so-called cellulose fluff pulp, for example.

Absorbent articles including a mixture of super absorbents and fluff pulp are previously known. With regard to the liquid-containing capacity, these articles present absorption values relating in principle to the proportion between the absorbent capacity of the incorporated components, whereas the liquid-transmitting capacity of these articles has shown itself to be insufficient.

At first, the manufacturers of absorbent articles intended for single use seemed to be very optimistic when faced with the opportunities associated with super absorbents, but despite great efforts during a period of at least ten years, no one has so far succeeded in the development of commercially marketable products with regard to manufacturing costs and total absorbency.

With the present invention, however, there has been achieved an absorption material intermixed with highly absorbent material, which composite absorption material has proved superior to previously known articles of this type.

An absorption material in accordance with the invention is primarily distinguished in that it comprises 70–95% of at least one type of absorbing fiber, preferably of cellulose, 2–20% of a binder activated by heat and preferably in the form of bonding fibers, and 2–25% of a highly absorbent material; the absorption fibers and the highly absorbent material thereby being bonded into a coherent body with the aid of the binder.

When using the absorption material in accordance with the invention, it has most surprisingly been found that the liquid-transmitting capacity of this composite material is greater than that of the separate components forming part thereof.

In view of this fact, and considering also the small amount of the comparatively expensive, highly absorbent material incorporated, it has now been possible for the first time to achieve a commercially marketable absorption material with a mixed-in, highly absorbent material.

The cause of the synergetic effect yielded, i.e. the transmitting capacity increasing upon addition of highly absorbent material, has not been fully established.

A possible explanation could be the fact that the highly absorbent material, which is bonded in the voluminous network structure formed by the absorption fibers and the binder, contributes to a reduction in size of the capillary ducts in this binding structure.

Figure 2:
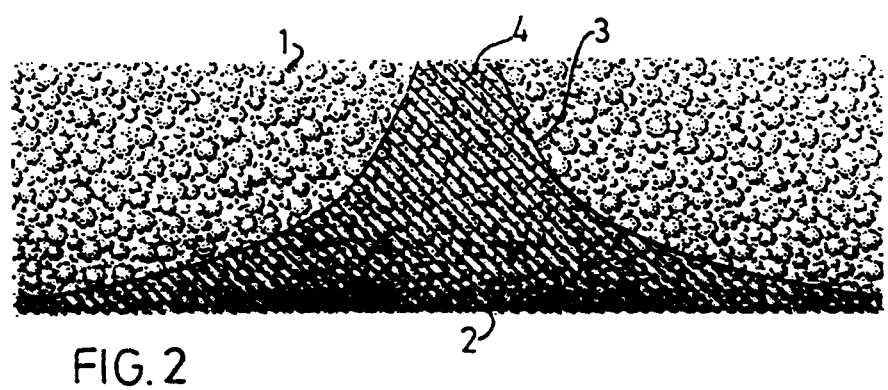
Figure 3:
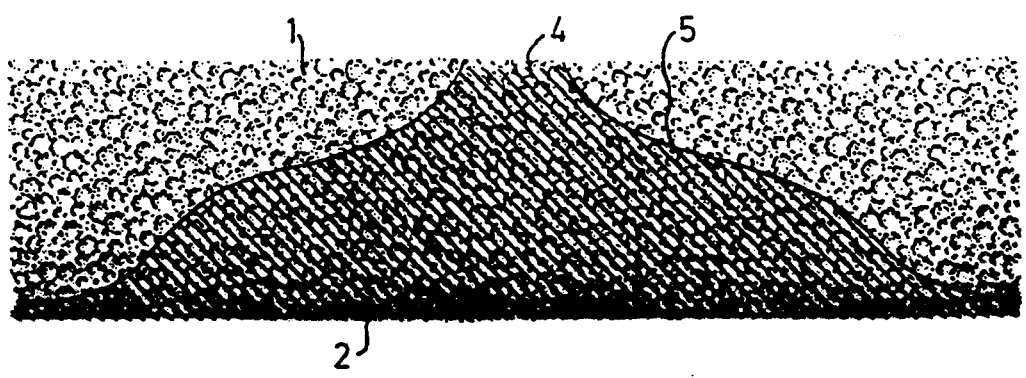

The invention will be described in more detail below with reference to the accompanying drawing, in which FIG. 1 is a cross-sectional view through an absorption body made of the inventive absorption material;

FIG. 2 shows the cross-section of FIG. 1 but provided with a distribution image of liquid absorbed in the absorption body; and FIG. 3 is a cross-sectional view corresponding to that of FIG. 2 through an absorption body but having another density gradient.

The embodiment illustrated in FIG. 1 of an absorption body made of an absorbent material in accordance with the invention is constructed of papermaking fibers in the form of so-called fluff pulp and bonding fibers such as, for example, those marketed under the trade name PULPEX by the U.S. company Hercules, as well as highly absorbent material such as, for example, that marketed under the trade name SANWET by the Japanese company Sanyo.

The bonding fibers will melt at their binding temperature and are thereby bonded together with the absorption fibers, obtaining in this way an absorption body which is comparatively shape-stable both in its wet and in its dry state, and in which the intermixed, highly absorbent powder is bonded to the voluminous network structure of the material.

In FIG. 1 the side of the absorption body facing the wearer during use of the article is denoted by 1, and the opposed side by 2. The absorption fibers which are cellulose fibers in this case, are united by means of the bonding fibers. The absorption body is designed to have a density which increases gradually in the direction from the side surface 1 facing the wearer and towards the opposed side surface 2. By appropriately balancing this density gradient and by selecting the density desired for the two outer layers 1,2, an absorption body having the optimal absorbency properties with regard to its intended use can be obtained. The absorption body is airlaid, while adding in this connection the highly absorbent powder, the concentration of the powder in the direction of thickness of the absorption body varying so that the highest concentration is located at the side 2 facing away from the wearer using the article.

FIG. 2 illustrates the distribution of liquid, and thereby the density gradient in the direction of thickness of the inventive absorption body. Liquid has been supplied here to a so-called wetting point 4 in the low-density surface layer 1 facing the wearer. The value of the density within the region closest to the surface layer 1 is so low that the liquid is substantially spread in the direction towards the opposed surface layer 2, gaining in this way the advantage that the side or surface i facing the wearer will not be wetted but remains essentially dry with a pleasant feel to the wearer.

As liquid penetrates into the gradually denser compressed absorbent material in the absorption body, the lateral distribution of absorbed liquid accelerates; the highly absorbent intermixed powder contributing to this increased spread as well. Only after the layer closest to the side surface 2 facing away from the wearer has been saturated with liquid, the spread of liquid will be reversed in the direction from the latter layer and towards the side surface 1 facing the wearer, which side will therefore remain at least essentially dry until all other absorbent material in the absorption body has been saturated with liquid.

As already mentioned, the density gradient in an absorption body made in accordance with the invention may be selected with regard to the intended use of the absorption body. The liquid distribution profile 3 shown in FIG. 2, i.e. the distribution of liquid from the side surface 1 facing the wearer towards the opposed side 2 facing away from the wearer prior to the spread liquid in the direction away from already saturated zones and back to the side surface 1 facing the wearer, illustrates an essentially optimal distribution of liquid for use in e.g. sanitary napkins. Besides the selection of density gradient in the direction of thickness of the absorption body, made with regard to absorbency only, this density can also be selected with regard to the desired stability and softness of the finished product.

FIG. 3 illustrates an absorption body made in accordance with the invention and having a density gradient which is extremely well suited for absorbent articles containing large amounts of liquid, such as diapers for example. In absorbent articles for diapers, a high capacity of transporting liquid away from the wetting point 4 is in fact a vital point. In an absorption body made in accordance with the invention, this requirement is fulfilled by means of the density gradient and supply of highly absorbent powder, chosen for a distribution profile 5, designed as shown in FIG. 3. The density and concentration of highly absorbent powder increases more rapidly here in the direction away from the upper side 1 of the absorption body facing the wearer and downwards in comparison with the absorption body shown in FIG. 2.

The invention will also be elucidated below by means of the following example. 84% cellulose fluff pulp was airlaid together with 8% of bonding fibers and 8% of highly absorbent material. The admixture was heated to the binding temperature of the melting fibers, and was then compressed to a suitable density. The absorption body built up in this manner had a liquid-retaining capacity of 27 grams per gram of absorption material, and a liquid-transmitting capacity of no less than 18 grams of liquid per gram of absorption material.

These are extremely good absorption properties, which is elucidated by the comparison with an absorption body of fluff pulp and bonded with the binder to the same density, which had a liquid-retaining capacity of 14 grams per gram of absorption material and a liquid-transmitting capacity of only 11 grams of liquid per gram of absorption material.

The inventive, highly absorbent material in itself had a liquid-retaining capacity of 32 grams per gram of absorption material, and a negligible liquid-transmitting capacity.

The invention is not restricted to the embodiments and the example described herein, but a plurality of modifications are possible within the scope of the following claims.

The absorption body can have substantially the same density throughout its entire volume. With such a performance there can be achieved a liquid distribution gradient by varying the concentration of highly absorbent material.

Alternatively, the absorption body can consist of several separate layers having varying degrees of concentration of highly absorbent material.

We claim:

1. Absorption material for use in diapers, sanitary napkins or wound dressings, which comprises 70-95% of at least one type of absorbing fibers, 2-20% of bonding fibers activated by heat, and 2-25% of a highly absorbent material, wherein the material has been compressed to produce an absorbent body, and all the bonding fibers are heat-fused and thus bond the absorbing fibers and the highly absorbent material into a coherent body which has a linearly continuous density gradient in a direction parallel to its thickness.

2. Absorption material according to claim 1, which comprises 80-90% of said at least one type of absorbing fibers, 4-12% of the bonding fibers, and 6-12% of the highly absorbent material.

* * * * *